United States Patent [19]

Barbee

[11] Patent Number: 4,791,811
[45] Date of Patent: Dec. 20, 1988

[54] DEPOSIT THICKNESS MEASUREMENT

[75] Inventor: James G. Barbee, San Antonio, Tex.

[73] Assignee: Southwest Research Institute, San Antonio, Tex.

[21] Appl. No.: 79,685

[22] Filed: Jul. 29, 1987

[51] Int. Cl.⁴ ............................................. G01M 15/00
[52] U.S. Cl. .................................... 73/119 R; 324/551
[58] Field of Search ................ 73/119 R; 324/65 R, 324/553, 554, 551

[56] References Cited

U.S. PATENT DOCUMENTS 3,199,023 8/1965 Bhimani ............................ 324/551
3,253,217 5/1966 Voltmann ........................ 324/65 R Primary Examiner—Jerry W. Myracle
Attorney, Agent, or Firm—Hamilton, Smith & Clarkson

[57] ABSTRACT

A system for determining the thickness of an oxide deposit on a conductive surface by applying a voltage across the deposit while measuring the dielectric breakdown of the layer at various points. An electrode mechanism containing a first electrode can be positioned at any point on the surface of the deposit with a high degree of accuracy. A second electrode is defined by a contact which is electrically coupled to the conductive surface. With the first electrode positioned at a point on the deposit, a ramped voltage is applied across the electrodes. An analog dielectric breakdown detection circuit monitors electrode voltage until dielectric breakdown occurs. At the point in time of dielectric breakdown of a deposit, the voltage across the deposit decreases sharply, approaching a short circuit condition. The dielectric breakdown detection circuit, however, maintains the maximum voltage attained, which is represented as the true breakdown voltage for the point being tested. The dielectric breakdown detection circuit comprises comparitor circuitry for determining if the particular point being tested exhibits normal dielectric breakdown characteristics or if the point represents a region of electrical conductivity. The data obtained is then stored and is subsequently processed to obtain an indication of the thickness of the deposit.

7 Claims, 3 Drawing Sheets

DEPOSIT THICKNESS MEASUREMENT

STATEMENT OF GOVERNMENTAL INTEREST

The U.S. Government has rights in this invention pursuant to Contract No. DAAK70-85-C-0007. The United States Government has a nonexclusive, nontransferable, irrevocable, paid-up license to practice or have practiced for or on behalf of the United States Government this invention throughout the world.

FIELD OF THE INVENTION

The present invention relates generally to the field of deposit thickness measurement. More particularly, the present invention provides a method and apparatus for automatically measuring the thickness of electrically insulative deposits on electrically conductive surfaces, such as the varnish-like deposits produced by fuels on heated engine components.

BACKGROUND

One of the problems encountered in systems employing hydrocarbon fuels is the build-up over time of thermal oxide derived varnish-like deposits on the surfaces of combustion chambers and components of the fuel distribution network. A number of testing methodologies have been used to measure such fuel deposits. For example, the jet fuel thermal oxidation test (JFTOT) is a test which is used to determine the deposit forming characteristics of jet fuels or other fuels. In this test, jet fuel is passed over a heated aluminum tube and deposits accumulate on the tube as a function of fuel quality, time, and tube temperature. The fuel is then given a rating based on the amount of deposit which accumulates on the rod over a fixed period of time. The JFTOT visual rating, using a light box with color standards, is the most commonly used rating method. While this visual rating method is suitable for certain types of fuel deposit evaluations, it has several inherent limitations. The rating scale has a very narrow dynamic range, since a deposit can only be rated into one of six categories (0,1,2,3,4,4+). Furthermore, the results are somewhat subjective, since each operator assigns the rating based on his individual perception of the "best match" to the color standard. For example, a thin, dark colored deposit could be given the same rating as a thicker but lighter colored deposit.

To overcome some of the limitations of the visual rating, a photo optical measuring device, known as a Tube Deposit Rater (TDR) is sometimes used. The TDR eliminates some of the problems associated with operator subjectivity and it allows a much wider rating scale of 0–50 measurement units. However, the TDR method does not overcome any of the other problems common to visual rating, such as the effects of deposit color or texture, and the TDR is incapable of directly producing deposit thickness, volume or mass data.

Another optical method for measuring the thickness of the deposits is based on the use of a transmission electron microscope (TEM). In this method the electron microscope is used to obtain an accurate indication of the actual thickness of the deposit on a cross-section of the aluminum tube. Although the TEM method provides a high degree of accuracy, it is extremely time consuming and expensive. Therefore, it is not feasible as an economical method for routine testing of fuels.

A number of electrical techniques for measuring the thickness of various types of deposits have been shown in the prior art. For example, a prior electrical method for measuring the thickness of an oxide deposit is shown in U.S. Pat. No. 4,495,558, issued to Cath. In this system, the thickness of an electrically insulative metal oxide material deposited on a conductive material is measured by reducing the metal oxide in an electrochemical cell while continuously measuring the cell voltage. A mathematical relationship between the cell voltage change and elapsed time of electrolytic reduction serves as a means for determining the thickness of the oxide coating.

U.S. Pat. No. 3,787,457, issued to Rogers discloses an apparatus and method for measuring the thickness of thin film on a nondestructive basis using an inductive bridge operating in its linear portion of unbalance and with an offsetting potential summed with the output of the bridge and with the bridge being fed with a precise amplitude and frequency signal. This system is calibrated relative to a first known thickness and then succeeding measurements of thin films are related to this known thickness.

The method and apparatus of the present invention, described in greater detail below, provides an effective technique for measuring the thickness of electrically insulative deposits based on the dielectric breakdown voltage of the deposit. In this measurement technique, the dielectric breakdown voltage is used as an indication of the thickness of the deposit. The dielectric breakdown method promises to be an effective, economical means for obtaining a measurement of deposit thickness. One of the difficulties encountered in this method, however, is that the deposit must be electrically insulative. Therefore, the measurements obtained in certain electrically conductive deposits produce spurious data which must be eliminated. The method and apparatus of the present invention provides a means for overcoming this difficulty, as described in greater detail below.

SUMMARY OF THE INVENTION

The present invention provides a system wherein the thickness of an oxide deposit on a tube can be determined by measuring the dielectric breakdown of the layer at various points on the tube. The tube to be tested is mounted in a carriage mechanism which has provisions for rotating the tube from 0 to 360 degrees. An electrode mechanism containing a first electrode can be positioned at any longitudinal point on the surface of the tube with a high degree of accuracy. A second electrode is defined by a contact which is electrically coupled to the tube. With the first electrode positioned at a point on the deposit, a ramped voltage varying from 0–1500 volts is applied across the electrodes. An analog dielectric breakdown detection circuit monitors electrode voltage until dielectric breakdown occurs. At the point in time of dielectric breakdown of a deposit, the voltage across the deposit decreases sharply, approaching a short circuit condition. The dielectric breakdown detection circuit, however, maintains the maximum voltage attained, which is represented as the true breakdown voltage for the point being tested. The dielectric breakdown detection circuit comprises comparitor circuitry for determining if the particular point being tested exhibits normal dielectric breakdown characteristics or if the point represents a region of electrical conductivity. The data obtained is then stored and is subsequently processed to obtain an indication of the thickness of the deposit.

DETAILED DESCRIPTION OF THE PREFERRED EMBODIMENT

Figure 1A:
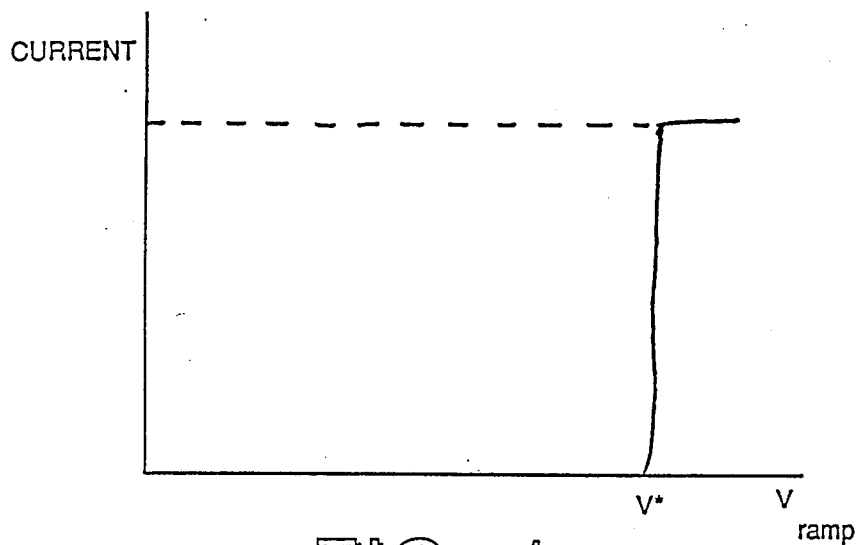
FIG. 1a is a graphical illustration of a thermal oxide deposit having a well defined dielectric breakdown point.
Figure 1B:
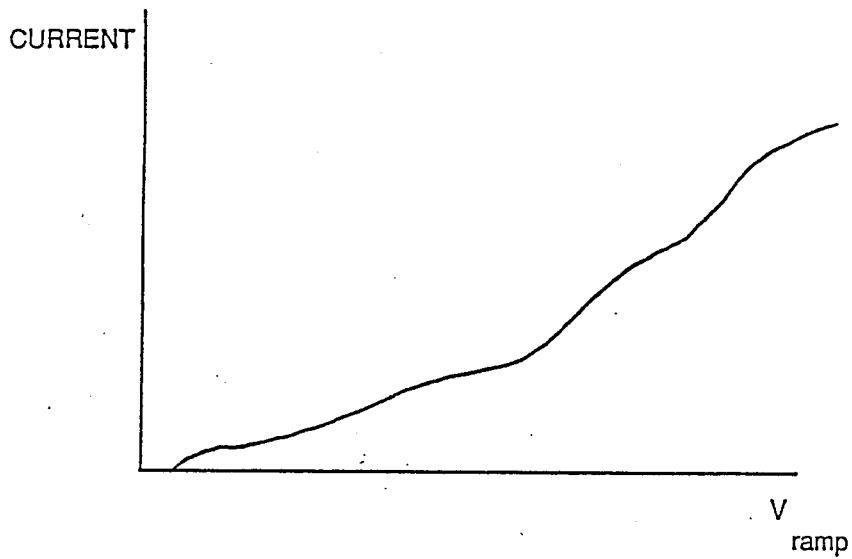
FIG. 1b is a graphical illustration of a thermal oxide deposit having a poorly defined dielectric breakdown point.

Referring to FIGS. 1a and 1b, mathematical relationships are shown relating the voltage applied to a thermally derived oxide deposit and the amount of current passed by the deposit. In FIG. 1a a curve 10 is shown illustrating the dielectric breakdown characteristics are shown for an ideally insulative deposit. The deposit passes no current until the voltage reaches a characteristic breakdown voltage, $V^*$, at which point the deposit passes current with essentially no resistance. In order to detect the dielectric breakdown point illustrated in FIG. 1a, the voltage applied to the test electrodes is "ramped" upward in a step-wise linear fashion to reach a predetermined maximum voltage over a predetermined length of time. In the preferred embodiment of the invention, the maximum voltage of approximately 1500 volts is achieved in about 3 seconds.

Some deposits contain regions which do not exhibit the "ideal" dielectric breakdown characteristics shown in FIG. 1a. The regions of non-ideal dielectric breakdown tend to exhibit voltage/current relationships such as that shown by curve 10a in FIG. 1b. These deposits do not exhibit a sharp increase in current flow at a particular point to indicate that dielectric breakdown has occurred. Instead, these deposits tend to pass increasing amounts of current as the voltage is raised. Such deposits are sometimes referred to as "creepers" since the current passed by the deposit "creeps up" with the increase in voltage. Deposits having regions of non-ideal dielectric breakdown, such as that shown in FIG. 1b, create difficulties for the use of automated deposit measurement systems, as will be discussed in greater detail below.

Figure 2:
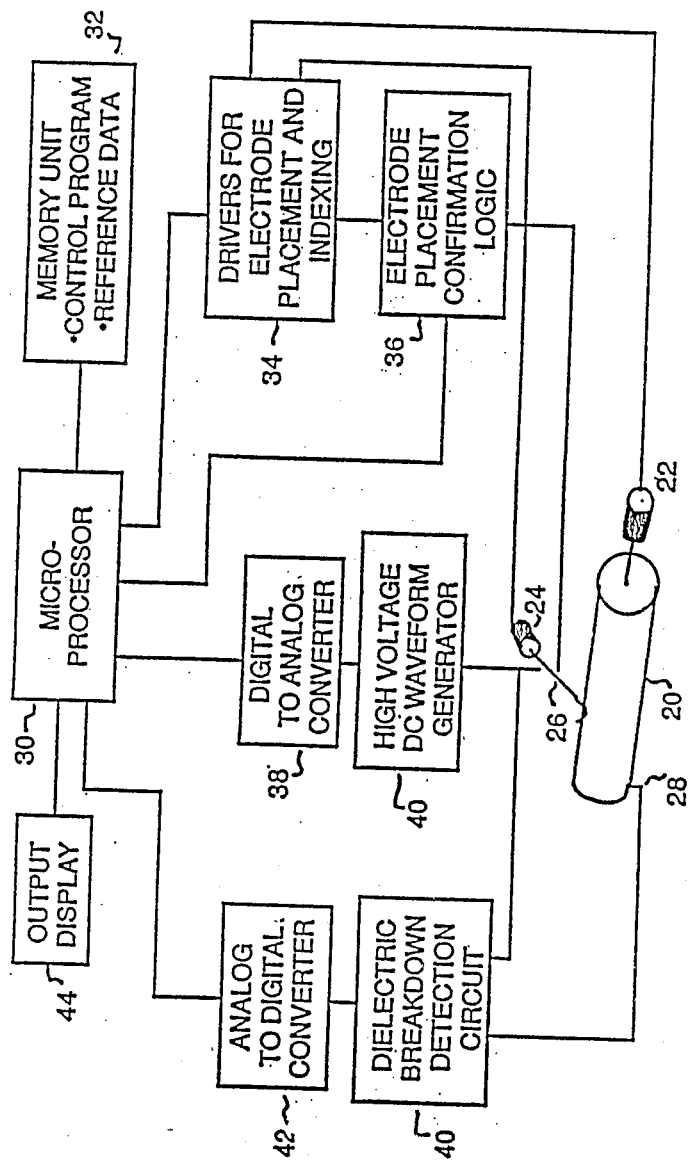
FIG. 2 is a schematic block diagram of a system for measuring the thickness of a thermal oxide deposit using the dielectric breakdown technique

FIG. 2 is a system block diagram of the automated system of the present invention for measuring deposit thickness using the dielectric breakdown technique. In this system, the deposit to be measured is carried on the surface of a tube 20 constructed of conductive material. The tube 20 is mounted in a carriage assembly comprising a rotating motor 22 and a stepper motor 24. The rotating motor 22 is capable of rotating the tube in small increments from 0 to 360 degrees. The stepper motor 24 is operably connected to an electrode assembly which holds a first electrode 26 which can be positioned at any longitudinal point on the surface of the tube 20. In the preferred embodiment of the invention, the electrode can be positioned longitudinally with an accuracy of 0.1 millimeters over a range of approximately 60 millimeters, which corresponds to a typical length of the oxide deposit on the tube. A second electrode 28 is defined by a contact which is electrically coupled to the conductive tube 20. The system is controlled by a microprocessor 30 which is responsive to a control program stored in a memory unit 32. The memory unit 32 also stores reference data for determining the thickness of the deposit after the entire tube has been mapped, as described in greater detail below.

The microprocessor 30 controls a circuit module 34 which contains drivers for controlling rotational and stepper motors 22 and 24, respectively. The position of the first electrode 26 is verified by an electrode placement confirmation logic module 36 which generates a placement confirmation feedback signal for the microprocessor 30. The microprocessor 30 also produces a voltage control signal which is provided to a digital-to-analog converter module 38 which, in turn, provides a control signal to a high-voltage DC wave form generator 40. The DC waveform generator 40 produces a stepwise, linear ramped voltage waveform to the first electrode 26. In the preferred embodiment, the waveform generator creates a voltage potential of approximately 1500 volts in a time period of approximately 3 seconds. The voltage and current characteristics of the deposit at the point being tested is measured by a dielectric breakdown detection circuit 40, described in greater detail below, which is connected across the first electrode 26 and the second electrode 28. When the detection circuit 40 measures a voltage which indicates the dielectric breakdown of the deposit, an output signal is produced and transmitted to the analog-to-digital converter 42 which, in turn, produces a digital data signal for use by the microprocessor 30. The microprocessor stores the dielectric breakdown characteristics of the deposit at that point and subsequently processes this information to obtain an indication of the deposit thichness at that point.

Operation of the rotational motor 22 and the stepper motor 24 of the carriage mechanism are controlled to allow the system to obtain a plurality of data points along the surface of the tube 20. With the tube in a stationary position, the position of the first electrode is incremented by the stepper motor 24 to cause the electrode 26 to measure the dielectric characteristics of the deposit along the longitudinal axis of the tube 20 to define a plurality of data points in the longitudinal direction of the tube. When the stepper motor reaches the edge of the deposit at one end of the tube, the rotational motor 22 causes the tube to rotate slightly and the stepper motor 24 then moves the first electrode 26 in the opposite direction along the longitudinal axis of the tube to define a second set of longitudinal data points. This process is repeated until the entire deposit on the surface of the tube 20 has been mapped. The operation of the rotational motor and the stepper motor can be controlled as described above to generate a plurality of data points to provide a map of the dielectric breakdown characteristics of the deposit at virtually any desired level of resolution. A carriage mechanism having the rotational and linear translation characteristics described above can be acheived through the use of a mechanical assembly from a commercially available standard computer printer.

The map of data points describing the dielectric breakdown characteristics of the deposit are processed by the microprocessor and the thickness of the deposit is determined by correlating the dielectric data for the plurality of points with reference data stored in the memory unit 32. In the preferred embodiment of the invention, the reference data contained in the storage unit is obtained by correlating the dielectric breakdown characteristics of a large number of deposits with the Transmission Electron Microscope method. The results obtained by the correlation of the data map of the deposit with the reference data is displayed on an appropriate display device 44 to provide an indication of the deposit thickness.

Figure 3:
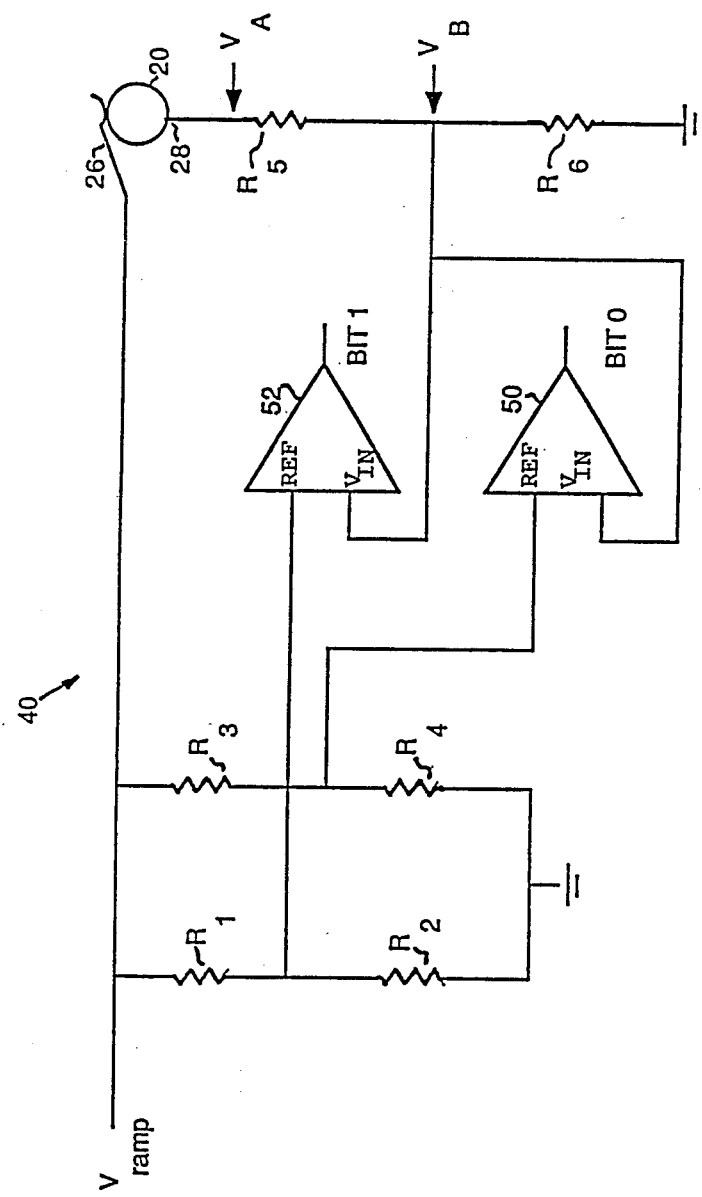
FIG. 3 is a schematic block diagram of the ramp voltage comparator circuit of the present invention.

As was discussed above, abnormal deposits containing regions of non-uniform resistivity can cause difficulties in the use of an automated deposit thickness measuring system, such as that shown in FIG. 2. The dielectric breakdown detection circuit 40 used in the preferred embodiment of the automated deposit thickness measuring system provides an effective means for eliminating spurious data points, as described in greater below. The preferred embodiment of the dielectric breakdown detection circuit 40 is shown in FIG. 3. The detection circuit is comprised of first and second comparators 50 and 52, respectively, which are connected to a resistive network which defines the anticipated dielectric characteristics of ideal and "creeper" deposit regions. One of the imputs to the detection circuit 40 is the ramped voltage waveform which is applied to first electrode 26. The ratio of the resistors R1 and R2 is selected to scale down the ramped voltage to a level which can be tolerated by the sensitive circuitry of the comparator and to provide a reference imput voltage to comparator 52 corresponding to the anticipated dielectric breakdown characteristics of an ideally insulative deposit. Likewise, the ratio of the resistors R3 and R4 is selected to provide appropriate voltage scaling and to provide a voltage reference input signal to comparator 50 corresponding to the anticipated dielectric breakdown characteristics of a nonideal deposit. The comparison input signal to each of the comparators is the voltage $V_b$ corresponding to voltage across the breakdown detecting resistor R6.

During the time period when the voltage is being ramped upward, the microprocessor 30 monitors the output of the comparators at predetermined time intervals to determine whether dielectric breakdown of the deposit has occurred. As was discussed above the ratios of the resistors in the resistor network are chosen to provide reference voltage input signals corresponding to the anticipated electrical behavior of ideal and nonideal deposits. In the preferred embodiment, these characteristics are defined by voltage corresponding to 40 percent and 4 percent, respectively, of the ramped input voltage. Comparator 50 determines if the voltage across the detecting resistor is greater than 4% of the ramped voltage. Comparator 52 determines if the voltage across the detecting resistor is greater than 40% of the ramped voltage. If the output of both the comparator circuits is low, then the microprocessor circuitry will continue to interrogate the output of each of the comparator circuits. The microprocessor continues to interrogate the circuits until either of the comparator circuits produces a positive output. Upon detection of a positive output, the microprocessor determines which of the comparitors produced the positive output. If comparator 50 and 52 both produce a positive output, then a dielectric breakdown event is indicated. However, if comparator 50 alone produces a positive output, then a conductive, or creeper deposit is indicated. If the output of the comparitors indicates that the test point exhibits normal dielectric breakdown characteristics, then the breakdown voltage of that point is stored for subsequent processing to determine deposit thichness. However, if the output of the comparitors indicates that the data point has nonideal dielectric breakdown characteristics, the deposit is indentified as abnormal and testing is terminated.

While the deposit thickness measurement system of the present invention has been described in connection with the preferred embodiment, it is not intended to limit the invention to the specific form set forth herein, but on the contrary, it is intended to cover such alternatives, modifications and equivalents as may be included within the scope and spirit of the invention as defined by the appended claims.

I claim:

1. An apparatus for measuring the thickness of an insulative layer deposited on the outer surface of a metal tube, comprising:
   a first electrode in contact with the surface of said insulative layer;
   a second electrode electrically coupled with said conductive surface;
   means for positioning said first electrode at a plurality of locations on said deposit;
   means for creating a voltage between said first and second electrodes at each of said locations, said voltage being increased in a timedependent, stepwise linear manner during the time that said first electrode is positioned at each location;
   means for measuring the voltage between said first and second electrodes at each said location and for producing a plurality of output signals in response thereto;
   means for detecting dielectric breakdown of the deposit at each said location and for correlating said output signals with the dielectric breakdown of said insulative deposit and for producing a plurality of data signals corresponding to the voltage between said first and second electrodes at which point said dielectric breakdown occurred for each said location; and
   means for correlating said plurality of data signals with the thickness of the deposit at each said data point.

2. An apparatus according to claim 1, said tube being mounted in a carriage mechanism, said means for positioning said first electrode comprising a stepper motor adapted to move said first electrode in a longitudinal direction with respect to said deposit on said tube.

3. An apparatus according to claim 2, said means for correlating said dielectric breakdown voltage with said deposit thickness further comprising means for identifying regions of said deposit having nonideal insulative characteristics.

4. An apparatus according to claim 3, said means for identifying regions of said deposit having nonideal insulative characteristics comprising first and second comparitor circuits, said first comparitor circuit producing a first comparitive output signal upon detection of a deposit having ideal insulative characteristics, said second comparitor circuit producing a second comparitive output signal upon detection of a portion of said deposit having nonideal deposit characteristics.

5. A method for determining the thickness of a layer of insulative material deposited on the surface of a metal tube, comprising the steps of:
   placing a first electrode in contact with the surface of said insulative layer at a plurality of locations on said layer;

electrically coupling a second electrode with said conductive surface;

creating a voltage between said first and second electrodes at each of said locations, said voltage being increased in a time-dependent, step-wise linear manner during the time that said first electrode is positioned at each location;

measuring the voltage between said first and second electrodes at each said location and producing a plurality of output signals in response thereto;

detecting dielectric breakdown of the deposit at each said location and correlating said output signal with the dielectric breakdown of said insulative deposit and producing a plurality of data signals corresponding to the voltage between said first and second electrodes at which point said dielectric breakdown occurred for each said location; and correlating said plurality of data signals with the thickness of the deposit at each said data point.

6. The method according to claim 5, said step of correlating said dielectric breakdown voltage with said deposit thickness further comprising the step of identifying regions of said deposit having nonideal insulative characteristics.

7. The method according to claim 6, said step of identifying regions of said deposit having nonideal insulative characteristics comprising the step of measuring the voltage between said first and second electrodes at each said location during the time said ramped voltage is being increased in said linear manner and correlating said voltage with known voltage characteristics of ideally insulative deposits.

* * * * *